United States Patent [19]
Jaeger, Jr. et al.

[11] Patent Number: 5,885,255
[45] Date of Patent: Mar. 23, 1999

[54] PROTECTIVE NEEDLE COVER

[76] Inventors: Cletus Wilfred Jaeger, Jr., 2739 N. W. 108th Ter., Sunrise, Fla. 33322; Laura Rivera Cuevas, 4640 N. W. 7th St., Miami, Fla. 33126

[21] Appl. No.: 360,109

[22] Filed: Dec. 20, 1994

[51] Int. Cl.$^6$ ..................................................... A61M 5/00
[52] U.S. Cl. ........................... 604/192; 604/198; 604/263
[58] Field of Search ..................... 604/263, 198, 604/192, 187, 199

[56] References Cited

U.S. PATENT DOCUMENTS

| | | | |
|---|---|---|---|
| 3,354,881 | 11/1967 | Bloch | 604/198 |
| 4,392,859 | 7/1983 | Dent | 604/198 |
| 4,416,663 | 11/1983 | Hall | 604/199 X |
| 4,469,482 | 9/1984 | Lissenburg et al. | 604/187 |
| 4,735,618 | 4/1988 | Hagen | 604/192 |
| 4,867,172 | 9/1989 | Haber et al. | 128/763 |
| 4,892,521 | 1/1990 | Laico et al. | 604/192 |
| 5,051,240 | 5/1991 | Soproni et al. | 604/192 |
| 5,078,697 | 1/1992 | Rammler | 604/198 |
| 5,122,123 | 6/1992 | Vaillancourt | 604/192 |
| 5,151,088 | 9/1992 | Allison et al. | 604/192 |

*Primary Examiner*—John D. Yasko
*Attorney, Agent, or Firm*—Robert L. McKellar

[57] ABSTRACT

The instant invention pertains to a flexible needle cover which surrounds a hypodermic needle on a syringe so that when the syringe is used the flexible needle cover retracts to expose the needle and after use the flexible needle cover returns back to its original shape covering the needle. The flexible needle cover of the instant invention is a bulb shaped elastomeric material that is capable of retracting during use with the application of slight pressure and returning to its original shape after the release of the pressure.

5 Claims, 2 Drawing Sheets

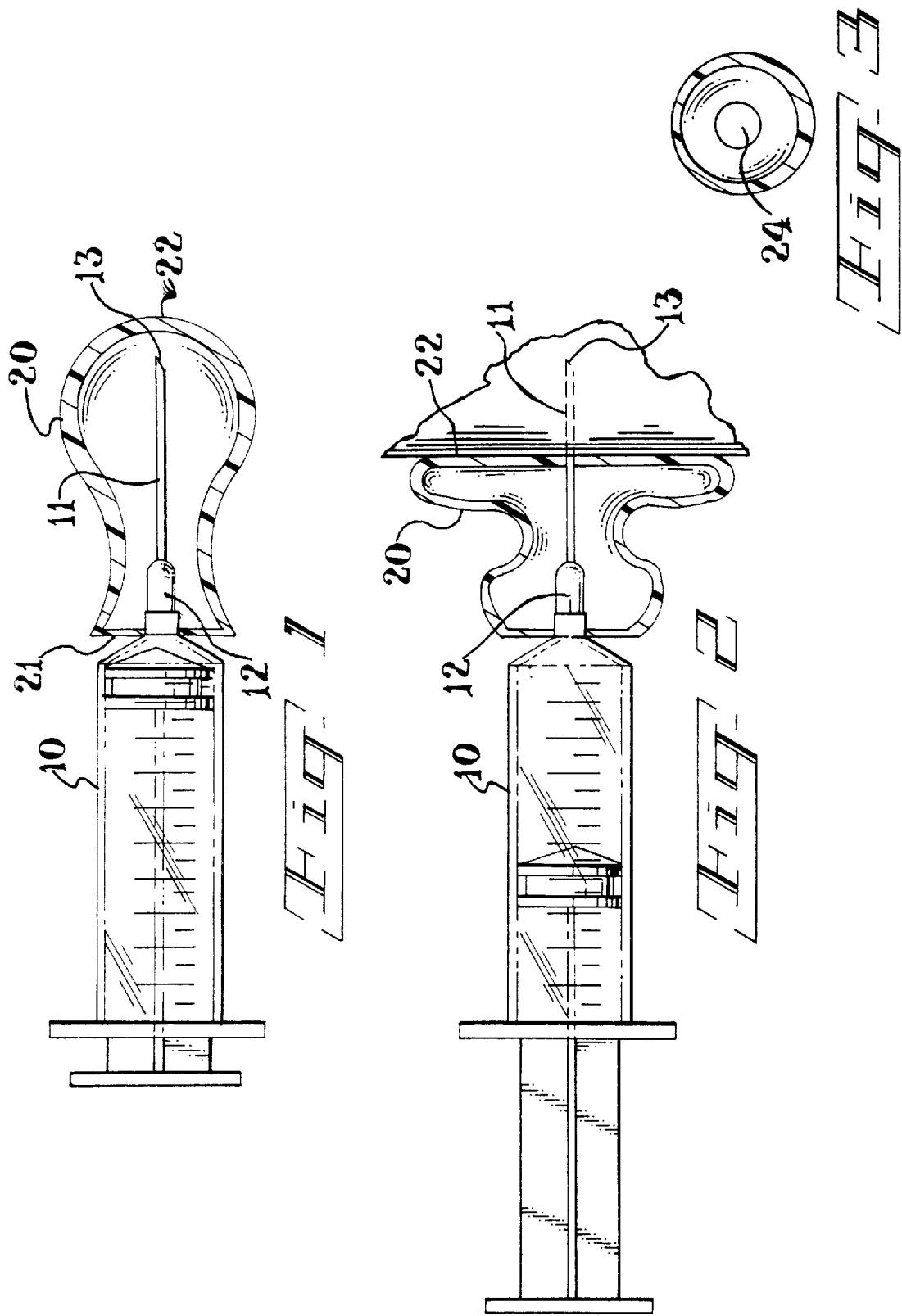

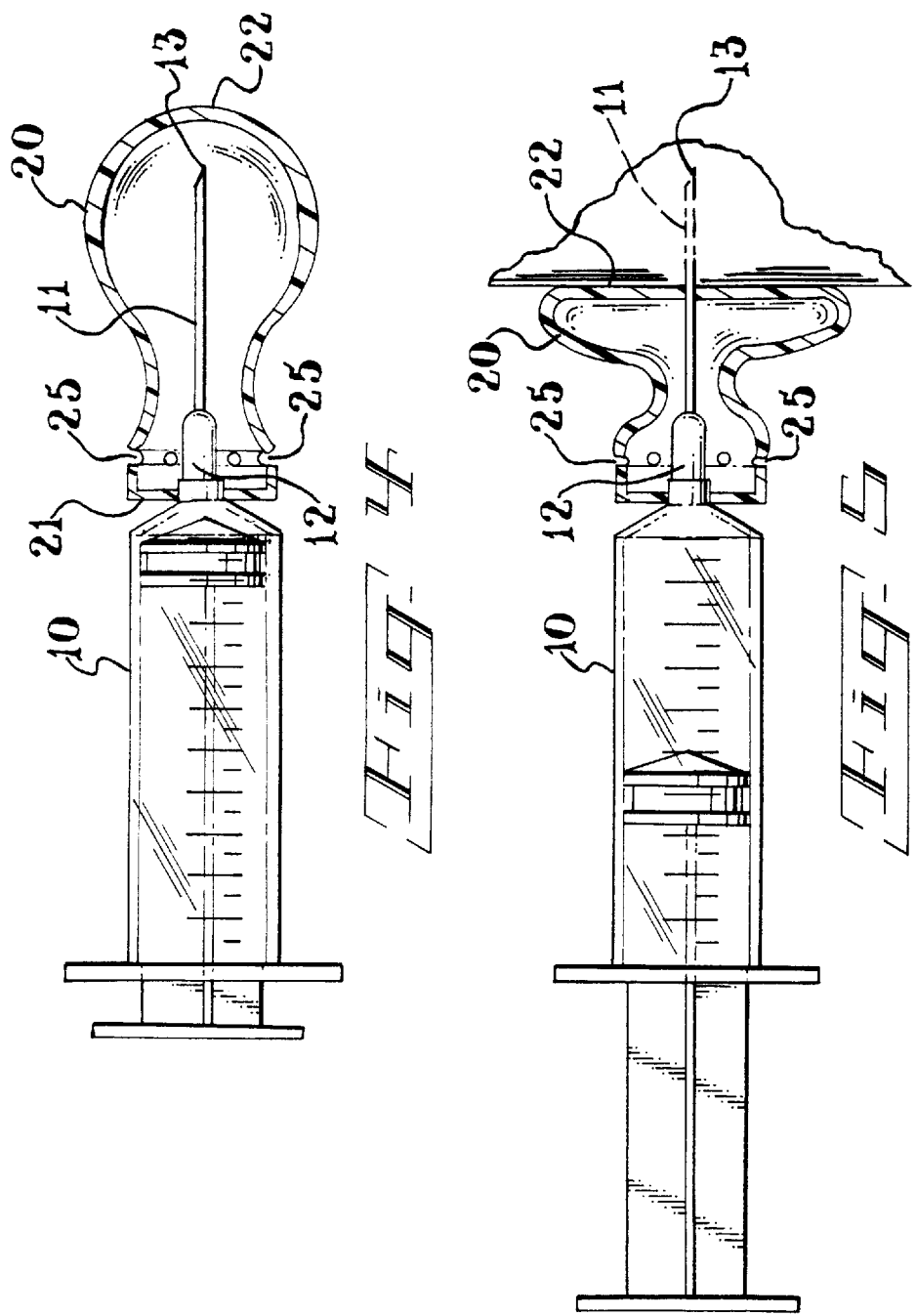

PROTECTIVE NEEDLE COVER

BACKGROUND OF THE INVENTION

Exposure to and contact with syringes contaminated with bodily fluid has become highly dangerous, resulting in the potential transmission of diseases through such contact. Thus, it has become desirable to cover the needle on the syringe to prevent accidental contact with the needle both before and after use. Procedures have been established for either capping of the syringe or disposal in such a manner to reduce accidental contact. However, even with these procedures, accidental contact continues to occur. Various caps have been designed to meet this need. For example in U.S. Pat. No. 5,05,240 to Soproni et al. there is shown a collapsible sheath covering the needle. However, this collapsible sheath is quite complex in design containing numerous bellows which allow it to retract. It also must be made of transparent material to enable one to properly maneuver the needle through the sheath for use of the syringe. Further, use of the syringe is complicated by the misalignment of the tip of the sheath with the tip of the needle.

It is an object of this invention to provide a protective needle cover which automatically shields the needle both before and after use and requires no action on the part of the user to remove or replace the protective shield for use.

SUMMARY OF THE INVENTION

The instant invention pertains to a flexible needle cover which surrounds a hypodermic needle on a syringe so that when the syringe is used the flexible needle cover retracts to expose the needle and after use the flexible needle cover returns back to its original shape covering the needle. The flexible needle cover of the instant invention is a bulb shaped elastomeric material that is capable of retracting during use with the application of slight pressure and returning to its original shape after the release of the pressure.

BRIEF DESCRIPTION OF THE DRAWINGS

FIG. 1 illustrates a syringe and needle assembly equipped with the invention in its unused state.

FIG. 2 illustrates a syringe and needle assembly equipped with the invention in the process of an injection.

FIG. 3 illustrates a cross-sectional view of the proximal end of the flexible needle cover.

FIG. 4 illustrates an alternative embodiment of the syringe and needle assembly equipped with the invention in its unused state.

FIG. 5 illustrates an alternative embodiment of the syringe and needle assembly equipped with the invention in the process of an injection.

THE INVENTION

As seen in FIGS. 1 and 2 the instant invention is a syringe 10 and needle 11 assembly wherein said hypodermic needle 11 is encompassed by a flexible needle cover 20. The flexible needle cover 20 of the instant invention is a hollow bulb shaped elastomeric material that is capable of retracting during use with the application of slight pressure and returning to its original shape after the release of the pressure.

The proximal end 21 of the flexible needle cover 20 is substantially flat and generally circular and has a centrally disposed orifice 24 (FIG. 3). The diameter of the orifice 24 is sufficient so that the flexible needle cover 20 may extend over the syringe 10 at the needle hub 12. The proximal end 21 of the flexible needle cover 20 may be slightly conical to follow the shape of typical needle hubs. The flexible needle cover 20 is adhered to the syringe 10 by suitable adhesion means such as adhesives, pressure-sensitive adhesives, or mechanical means such as ribs or bands.

As can be seen in FIGS. 4 and 5 there can be located at or near the proximal end 21 of the flexible needle cover 20 at least one, preferably two, vent holes 25 to allow internal air to escape when pressure is applied as the syringe 10 is used. As seen in FIGS. 1 and 2, when there are no vent holes present in the flexible cover 20, the cover acts as a sterile barrier to the needle 11, providing a sterile environment to the needle until it is used.

The length of the flexible needle cover 20 is sufficient to cover and extend slightly past the needle tip 13. The flexible needle cover 20 gradually increases in diameter from the locality near the proximal end 21 of the cover 20 to a imperforate substantially semispherical portion which forms the distal end 22 of the cover 20 as shown best in FIG. 1. The flexible needle cover 20 is hollow with the inside passageway, beginning at the orifice 24 gradually increasing in diameter following the general shape of the exterior of the flexible needle cover 20. The flexible needle cover 20 will typically have thickness of less than 2 mm, preferably less than 1 mm. A cover 20 which is too thick will not be sufficiently flexible to allow the needle to penetrate during use. On the other hand, if the cover 20 is too thin, then accidental exposure may occur due to the excessive flexibility that may result.

The flexible needle cover 20 is formed of a flexible, resilient elastomeric material. The elastomeric material should be a non-coring rubber, having a low modulus, high elongation and high tear strength. A non-coring rubber is necessary to prevent rubber plugs from being formed as the needle penetrates the rubber. A low-modulus is necessary to allow for the needle 11 to pass easily through the flexible needle cover 20. However if the modulus is too low the needle 11 may pass through too easily again increasing the risk of exposure to the needle 11 by the user. One skilled in the art will be able to select an appropriate modulus that will provide sufficient flexibility for use but still provide the desired level of protection to the user. It is also necessary for the rubber to have a high elongation and high tear strength to provide for easy molding and removal of the flexible needle cover 20. If the elongation and/or tear strength are too low, one would not be able to remove the flexible needle cover 20 from the mold without damage. Preferably the rubber should have a modulus in the range of 35 to 45, an elongation of greater than 350% at elongation break, a tear strength of greater than 150 ppi and a tensile strength of greater than 1000 psi. Suitable elastomers include synthetic rubbers such as silicone rubbers, and organic rubbers, i.e. polyurethanes, polyacrylates and others; and natural rubbers such as latex so long as the elastomers are non-coring and have a low moduli.

Syringe 10 and needle 11 assemblies containing the flexible needle cover 20 may be used by placing the cover 20 in contact with the skin and applying slight force to allow the needle to penetrate the cover 20 and the skin. When the needle 11 is withdrawn from the skin, the cover 20 returns to its original shape. The flexible needle cover 20 of the instant invention allows one to use a syringe 10 and needle 11 assembly without the risk of accidental exposure to contaminated bodily fluids during and after use. The user does not have to remove or replace the cover 20 at any time before, during or after use.

What is claimed is:

1. A hypodermic needle and syringe assembly having adhered to the syringe a single bodied hollow bulb shaped flexible needle cover said needle cover comprising a substantially flat and generally circular proximal end containing a centrally disposed orifice;

a substantially semispherical distal end; and said flexible needle cover being produced from a non-coring, low modulus elastomeric material;

wherein said flexible needle cover provides a sterile barrier to the needle and is capable of retracting during use of the hypodermic needle syringe with application of slight pressure and returning to its original shape after release of the pressure.

2. A hypodermic needle syringe assembly as claimed in claim 1 wherein the flexible needle cover is produced from a non-coring, low modulus silicone rubber.

3. A hypodermic needle syringe assembly as claimed in claim 1 wherein the flexible needle cover is produced from a non-coring, low modulus synthetic organic rubber.

4. A hypodermic needle syringe assembly as claimed in claim 1 wherein the flexible needle cover is produced from a non-coring, low modulus natural rubber.

5. A hypodermic needle syringe assembly as claimed in claim 2 wherein the silicone rubber has a modulus of 35 to 45, an elongation of greater than 350% at break, a tear strength of greater than 150 ppi and a tensile strength of greater than 1,000 psi.

* * * * *